United States Patent [19]

Osborn

[11] 4,083,245

[45] Apr. 11, 1978

[54] VARIABLE ORIFICE GAS FLOW SENSING HEAD

[75] Inventor: John J. Osborn, Tiburon, Calif.

[73] Assignee: Research Development Corporation, San Francisco, Calif.

[21] Appl. No.: 779,557

[22] Filed: Mar. 21, 1977

[51] Int. Cl.² ............................................. G01F 1/22
[52] U.S. Cl. ................................................... 73/207
[58] Field of Search ......................... 73/207, 210, 211; 128/2.08

[56] References Cited

U.S. PATENT DOCUMENTS

| | | | |
|---|---|---|---|
| 2,989,866 | 6/1961 | Widell | 73/207 |
| 3,232,288 | 2/1966 | Krobath | 128/2.08 |
| 3,989,037 | 11/1976 | Franetzki | 73/207 |
| 4,006,634 | 2/1977 | Billette | 73/207 |

*Primary Examiner*—Herbert Goldstein

*Attorney, Agent, or Firm*—Flehr, Hohbach, Test, Albritton & Herbert

[57] ABSTRACT

A gas flow meter employing means for obtaining a differential pressure across a resistance orifice in a line of gas flow. Although flow through the orifice may be turbulent thus making the differential pressure non linear with respect to the amount of flow, the effect of that turbulence is offset by the provision of a hinged flap within the orifice which opens upon increase in gas flow thereby lowering the orifice's resistance to that flow. Because of the variable resistance orifice the resultant pressure differential is linear with respect to the amount of flow. The differential pressure is sensed by pressure tubes disposed on opposite sides of the orifice and the hinged flap is arranged to flex over the downstream pressure tube so as to protect it from eddy currents. Moreover, the flap is hinged at the top and opens from the bottom whereby free liquid may pass through the orifice without any significant change in calibration.

5 Claims, 5 Drawing Figures

2

VARIABLE ORIFICE GAS FLOW SENSING HEAD

BACKGROUND OF THE INVENTION

The measurement of respiratory flow in patients having respiratory difficulties is extremely important. While there are numerous present methods of measuring such flow, each of them suffers from serious defects. The most common method employed to measure such flow is a resistance pneumotachograph of which the most popular is the Fleisch unit. The resistance pneumotachograph utilizes the principal of measuring a differential pressure caused by an air flow across a resistance in a tube. Prior to the pneumotachograph such resistance was provided by the usual simple orifice. However, with the usual orifice provided for such measurements, flow at the orifice itself becomes turbulent rather than laminar. With turbulent flow, the resistance increases with the flow and the differential pressure measurement does not produce a linear representation of the actual flow. But when flow is laminar, the resistance remains almost constant over a wide range of flow. In order to maintain the flow through the resistance laminar, the Fleisch-type resistance pneumotachograph comprises essentially many small parallel tubes which not only produce the resistance to the flow but also laminate that flow thereby eliminating the effects of turbulence. By measuring the pressure on each side of the small parallel tubes the amount of flow can be determined. Since the flow is laminar, the resistance to flow is constant over a wide range and the differential pressure measurement then is a linear representation of the actual flow of gas.

While the resistance pneumotachogrpah is highly advantageous from a theoretical point of view, it does have serious drawbacks including substantially large size and weight and the small tubes being subject to plugging by either mucus of moisture from the humid air way. Plugging from moisture can be eliminated by heating the device but the problems of mucus together with size and weight are serious and present a substantial drawback to the use of the pneumotachograph.

Other flow measuring devices have been employed for measuring flow at the mouth during pulmonary function testing. In devices for such short term tests there is frequently a large dead space volume and, in addition, they are frequently unstable when water is present in the system.

Still other attempts to measure respiratory flow have been made including the development of ultrasonic flowmeters, hot wire flowmeters, vortex counters and many others. Each of these has its own disadvantage.

SUMMARY OF THE INVENTION AND OBJECTS

The invention is incorporated in a sensing head which may be inserted in a gas flow tube. The sensing head is arranged for flow of gas horizontally therethrough and includes an orifice membrane which defines a single orifice and a single flap hinged at the top of the orifice. The flap is resiliently urged into closed position. As gas flow through the tube and the sensing head increases, the hinged flap opens thereby reducing the amount of resistance in the orifice. The reduction of resistance caused by opening the orifice offsets the increase of resistance caused by the increased turbulent flow.

It is, therefore, a general object of the present invention to provide an improved gas flow meter.

It is a further object of the present invention to provide such an improved gas flow meter wherein the size of the orifice increases with the amount of gas flow there through such that the overall resistance to that flow is held constant upon an increase in the amount of turbulent flow.

DETAILED DESCRIPTION OF THE PREFERRED EMBODIMENT

Figures 1, 2:
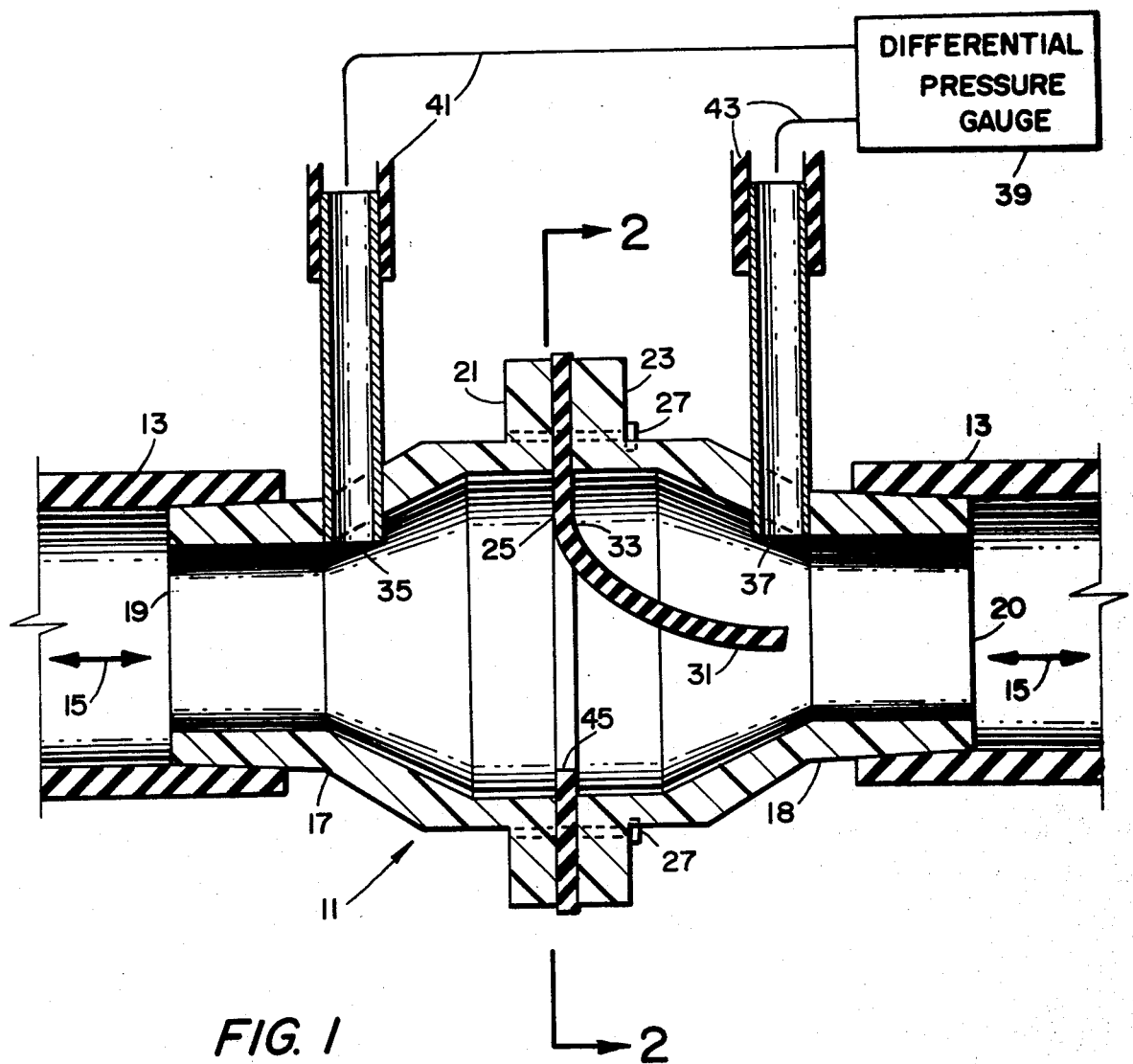
FIG. 1 is a longitudinal sectional view of the variable orifice gas flow sensing head in accordance with the invention.
FIG. 2 is a view along the lines 2—2 of FIG. 1 showing the shape of the flap in the orifice membrane.

Referring to the drawing a sensing head 11 is disposed in a gas flow line 13 through which gas may flow horizontally in the direction of the arrows 15. The head may include inlet and outlet portions 17,18 having ports 19 and 20, each of which carries a flange 21,23 for securing them together. An orifice membrane 25 is retained between the flanges 21,23 by means of screws 27 or the like.

As seen particularly in FIG. 2 the orifice membrane 25 defines an orifice 29 and flap 31 disposed therein. For convenience the orifice membrane may be formed of rubber or elastic material, the flap 31 being integral therewith to provide a resilient hinge area 33. Other means of providing a resilient closure for the flap 31 may, however, be provided within the spirit of the invention.

As shown particularly in FIG. 2 the shape of the orifice 29 is such that with relatively small gas flow, the orifice will be open but slightly thereby providing a relatively high resistance. As gas flow increases the flap is urged farther outward, as shown in FIG. 1. In this manner the orifice size increases and its resistance decreases as the flow therethrough increases. Thus while the flow through the orifice itself is turbulent and would ordinarily provide an increase in resistance with an increase in flow, an offsetting reduction in resistance is provided by the variable orifice. The resultant resistance at the orifice is therefore constant such that the relation between gas flow and differential pressure across that resistance is linear and the amount of flow can be read directly from a differential pressure gauge.

In order to read the gas flow in such a manner, pressure ports 35 and 37 are provided in the head 11 and are connected to a differential pressure gauge 39 by means of tubes 41 and 43 shown, in part, diagramatically.

As noted in FIG. 1 the pressure ports 35 and 37 and the hinge 33 of the flap 31 are located at the upper side of the sensing head. Conversely, the apex of the orifice is located at the lower side. With such an arrangement drops, or even streams, of water can pass through the bottom of the orifice at its apex 45 without causing any important change in the calibration of the flowmeter.

Moreover, it can be seen that when the flap 31 is flexed by reason of a high flow in the pressure head, the flap itself extends over the downstream pressure port (37 as shown in FIG. 1) thereby protecting it from eddys generated by the turbulent flow through the orifice. Protecting the downstream port from such eddys in this manner, not only eliminates a major source of noise in the pressure signals read by the head but also avoids a non-symmetrical Pitot tube effect which results from directly shielding the port.

In one embodiment of the invention constructed and utilized with excellent results, the orifice membrane 25 was constructed of a highly elastic medical grade silastic rubber with low hysteresis having a thickness of 0.9 mm. Referring to FIG. 2, the width of the flap, between the corners 47 and 49, was 1.5 cm., while the vertical distance from the apex 45 to the hinge 33 formed between the corners 51 and 53 was also 1.5 cm. The distance across the hinge was 0.6 cm. and the vertical distance from the hinge to the wide part of the flaps defined by the line between the points 47 and 49 was 0.6 cm. The width of the slit between the flap 31 and the orifice 29 was 0.7mm. Referring to FIG. 1, the diameter of the ports 19 and 20 was 1.1 cm.—slightly smaller than the length across the flap 31 in any direction.

In use of the flow sensing head shown and described and of earlier versions thereof, it has been found that a single hinged flap, as contrasted to two or more such flaps, provides pressure readings with considerably less noise. The single flap in the head is chosen to be slightly larger than the input and output ports so that in the event the flap should break off after long use, it will be trapped in the head itself and not pass on to the patient's lung. Moreover, the widest diameter of the flap 31 is off center in relation to the total area of the flap. With such a construction, should the flap break off at its hinge and wedge itself in the outflow tube, it will turn like a weathervane with its plane in line with the air flow. The airway, then, will not be obstructed.

Figure 3:
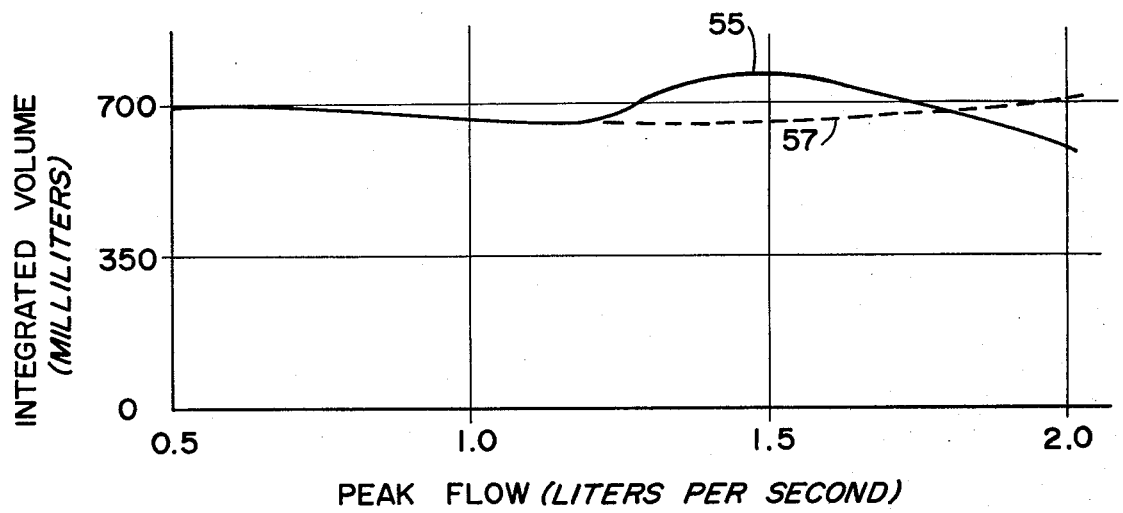
FIG. 3 is a diagram plotting peak-flow rate against volume measurement by flowmeter comparing the flow sensing head of the invention with that of an earlier known design.

Referring to FIG. 3, there is shown a comparison of the pressure sensing head of the invention with that of earlier known design. The earlier device was of the type employing a plurality of fingerlike flaps of varying length such that each flap had a different resistance to the flow. For the curves of FIG. 3, a piston pump having a true stroke volume of 0.7 liters was driven at different speeds to deliver a peak flow varying from 0.5 to 2.0 liters per second. The volume was measured by integrating the flow signals derived from the pressure sensing heads under consideration. The curve 55 shows the performance of the earlier design head and it can be seen that the measurements depart substantially from linearity at flow rates above 1.0 liter per second. The curve 57, showing the performance of the head shown and described herein, is clearly far more linear.

Figure 4:
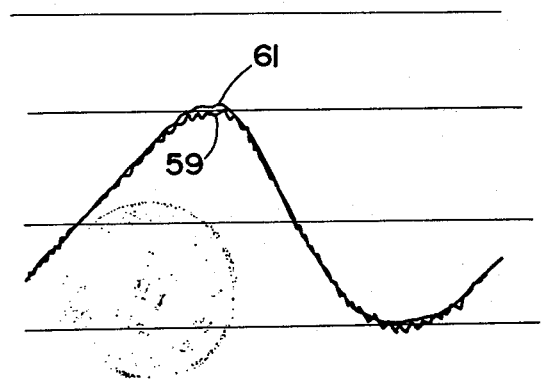
FIG. 4 is a diagram plotting actual flow against time using a linear flowmeter for one curve and the flow sensing head of the invention for the other.
Figure 5:
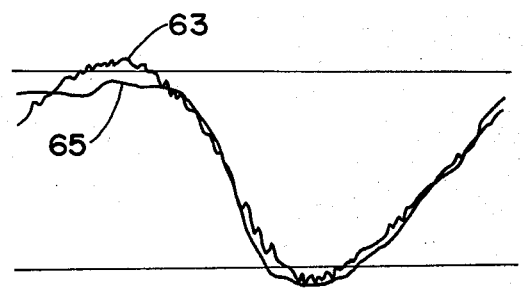
FIG. 5 is a diagram plotting actual flow against time using a linear flowmeter for one curve and a flow sensing head of an earlier known design for the other.

Still other comparisons were made with the same early device and the results are shown in FIGS. 4 and 5. In each of these figures a trace of the sensing head under consideration is superimposed over a trace from a standard reference flowmeter using the air flow from a piston pump driven in a sine wave with peak flow of 1 liter per second. The traces were recorded on an Electronics for Medicine DR-8 multichannel recorder, using a Statham P5-0.2D-350 unbounded strain-gauge differential pressure transducer. The standard reference flow transducer was a Fleisch #1 laminar flow differential pressure flow transducer, sold by Dynasciences (Division of Whittaker Corp.), connected to a similar Statham gauge.

Referring specifically to FIG. 4, trace 59 is of the standard reference flowmeter and trace 61 is of the flowmeter shown and described herein. In FIG. 5, trace 63 is of the standard and trace 65 is of the early device. Comparing FIGS. 4 and 5 it is seen that as flow approaches 1 liter per second the early device becomes unstable while that of the present invention closely tracks the standard reference.

In summary then, it is seen that the variable orifice gas flow sensing head of the present invention provides a way of measuring gas flow by differential pressure across a resistance with resultant curves much in accord with the resistance pneumotachograph. The sensing head of the present invention, however, avoids the difficulties which result in the use of the small tubes of the resistance pneumotachograph. Moreover, the gas flow sensing head of the present invention can be made considerably smaller, lighter and cheaper than other sensing heads and need not be heated. Because of the use of a simple orifice rather than the numerous small tubes of the resistance pneumotachograph it is substantially immune to clogging from water or mucus. The unit then is small, exceedingly light and stable over a wide range of air flow and temperatures. It is almost impervious to calibration changes from obstruction by water, mucus, or particulate material and can be made so economically that it can be disposable.

What is claimed is:

1. A gas flow sensing head comprising a housing having gas inlet and gas outlet ports, an orifice membrane disposed across the interior of said housing between said inlet and outlet ports, said orifice membrane being formed of an elastic material, said orifice membrane including a partially cutout portion defining an orifice and a flap integral with and hingably connected to the membrane and substantially coextensive with the orifice, said flap including sides which converge to form the narrowest portion of the flap at that portion thereof most remote from the hinged connection to the orifice membrane whereby the flow of gas through said housing varies the size of said orifice, said hinged connection being narrower than the widest portion of said flap and means disposed on each side of said orifice membrane for sensing the pressure thereat.

2. A gas flow sensing head as defined in claim 1 wherein said orifice membrane includes top and bottom sides, said hinged connection being at the top of said orifice membrane and said narrowest portion of the flap being at the bottom whereby liquid may pass through said orifice without interference with said hinge.

3. A gas flow sensing head as defined in claim 2 wherein said orifice membrane defines but a single flap.

4. A gas flow sensing head as defined in claim 1 wherein said flap being wide at its base and narrow at its apex, the elasticity of the hinge and the annular shape of the flap being so matched that the resistance across the orifice is constant over a wide range of flow.

5. A gas flow sensing head comprising a housing having gas inlet and gas outlet ports, an orifice membrane disposed across the interior of said housing between said inlet and outlet ports, said orifice membrane being formed of an elastic material, said orifice membrane having top and bottom sides and including a partially cut-out portion defining an orifice and a flap integral with and hingably connected to the membrane and substantially coextensive with the orifice, said hinge connection being at the top of said orifice membrane, said flap including sides which converge to form the narrowest portion of the flap at the bottom thereof whereby the flow of gas through said housing varies the size of said orifice and liquid may pass through said orifice without interference with the hinge, and means disposed on each side of said orifice membrane for sensing pressure thereat, said means for sensing pressure including a tube disposed on each side of the membrane, the tube on the outflow side of said membrane being disposed adjacent the top of said membrane whereby said flap may extend under the tube to protect it from eddies when the gas flow rate is high.

* * * * *